United States Patent [19]

Cole

[11] Patent Number: 5,102,788
[45] Date of Patent: * Apr. 7, 1992

[54] IMMUNOASSAY INCLUDING LYOPHILIZED REACTANT MIXTURE

[75] Inventor: Francis X. Cole, Stow, Mass.

[73] Assignee: Hygeia Sciences, Inc., Newton, Mass.

[*] Notice: The portion of the term of this patent subsequent to Jun. 5, 2007 has been disclaimed.

[21] Appl. No.: 344,575

[22] Filed: Apr. 28, 1989

Related U.S. Application Data

[63] Continuation-in-part of Ser. No. 275,656, Nov. 21, 1988, Pat. No. 4,931,385, which is a continuation of Ser. No. 747,605, Jun. 24, 1985, abandoned.

[51] Int. Cl.⁵ .............. G01N 33/535; G01N 33/546; G01N 33/553
[52] U.S. Cl. .................. 435/7.9; 435/188; 435/962; 435/963; 435/975; 436/518; 436/523; 436/525; 436/533; 436/534; 436/808; 436/826
[58] Field of Search ............. 435/7, 188, 810, 9, 435/962, 963, 975; 436/518, 523, 525, 533, 534, 808, 826

[56] References Cited

U.S. PATENT DOCUMENTS

| | | | |
|---|---|---|---|
| 2,908,614 | 10/1959 | Muggleton | 167/78 |
| 3,378,443 | 4/1968 | Cooper et al. | 167/78 |
| 3,423,290 | 1/1969 | Seamans, Jr. | 195/99 |
| 3,652,761 | 3/1972 | Weetall | 424/12 |
| 3,791,932 | 2/1974 | Schuurs et al. | 195/103 |
| 3,825,410 | 7/1974 | Bagshawe | 23/230 |
| 3,880,715 | 4/1975 | Schneider | 195/103 |
| 3,963,441 | 6/1976 | Dietrich | 23/253 |
| 3,987,159 | 10/1976 | Spona et al. | 424/12 |
| 4,017,597 | 4/1977 | Reynolds | 424/1.5 |
| 4,062,933 | 12/1977 | Wolfangel | 424/1 |
| 4,094,647 | 6/1978 | Deutsch et al. | 23/253 |
| 4,108,974 | 8/1978 | Wegfahrt et al. | 424/1 |
| 4,115,535 | 9/1978 | Giaever | 424/1 |
| 4,157,280 | 6/1979 | Halbert et al. | 195/127 |
| 4,169,012 | 9/1979 | Dawson et al. | 435/7 |
| 4,188,371 | 2/1980 | Weetal | 424/1 |
| 4,200,690 | 4/1980 | Root et al. | 435/7 |
| 4,206,200 | 6/1980 | Guthöhrlein et al. | 242/92 |
| 4,228,240 | 10/1980 | Dawson et al. | 435/188 |
| 4,230,664 | 10/1980 | Cais | 422/61 |
| 4,248,965 | 2/1981 | Mochida et al. | 435/7 |
| 4,256,833 | 3/1981 | Ali et al. | 435/7 |
| 4,273,868 | 6/1981 | Walter | 435/14 |
| 4,280,816 | 7/1981 | Elahi | 23/253 |
| 4,287,300 | 9/1981 | Gibbons et al. | 435/5 |
| 4,299,916 | 11/1981 | Litman et al. | 435/6 |
| 4,310,504 | 1/1982 | Derfler et al. | 424/1 |
| 4,340,395 | 7/1982 | Magers et al. | 23/230 |
| 4,343,896 | 8/1982 | Wolters et al. | 435/7 |
| 4,385,114 | 5/1983 | Güthlein et al. | 435/28 |
| 4,386,224 | 5/1983 | Deetman | 568/703 |
| 4,391,904 | 7/1983 | Litman et al. | 435/7 |
| 4,444,879 | 4/1984 | Foster et al. | 435/7 |
| 4,446,232 | 5/1984 | Liotta | 435/7 |
| 4,448,882 | 5/1984 | Brodbeck et al. | 435/188 |
| 4,457,916 | 7/1984 | Hayashi et al. | 424/101 |
| 4,458,014 | 7/1984 | Ebersole | 435/7 |
| 4,459,358 | 7/1984 | Berke | 436/170 |
| 4,459,359 | 7/1984 | Neurath | 436/507 |
| 4,486,530 | 12/1984 | David et al. | 435/7 |
| 4,503,143 | 3/1985 | Gerber et al. | 435/7 |
| 4,545,452 | 5/1985 | Jones et al. | 435/7 |
| 4,615,972 | 10/1986 | Gallacher | 435/7 |
| 4,659,666 | 4/1987 | May et al. | 435/188 |
| 4,681,782 | 7/1987 | Ozkan | 428/36 |
| 4,853,335 | 8/1989 | Olsen et al. | 435/7 |
| 4,859,612 | 8/1989 | Cole et al. | 436/533 |
| 4,931,385 | 6/1990 | Block et al. | 435/7 |

FOREIGN PATENT DOCUMENTS

| | | |
|---|---|---|
| 0042755 | 8/1988 | European Pat. Off. |
| 2541031 | 3/1977 | Fed. Rep. of Germany |
| 2712044 | 9/1977 | Fed. Rep. of Germany |
| 2388275 | of 0000 | France |
| WO79/00256 | 5/1979 | PCT Int'l Appl. |
| 554867 | 4/1977 | U.S.S.R. |
| 2049700 | 12/1980 | United Kingdom |
| 2062224 | 5/1981 | United Kingdom |

OTHER PUBLICATIONS

P. Nakane, "Preparation and Standardization of Enzyme-Labeled Conjugates", *Immunoassays in the Clinical Laboratory*, Alan R. Liss, Inc., pp. 81-87 (1979).

E. Engvall et al., "Immunochemical Techniques", in *Methods in Enzymology*, Part A, H. V. Vunakis et al., eds., Academic Press, New York, pp. 430-432 (1980).

P. K. Nakane et al., "Peroxidase-Labeled Antibody A New Method of Conjugate", *J. of Histochemistry and Cytochemistry*, vol. 22, No. 12, pp. 1084-1091 (1974).

M. Uotila et al., "Two-Site Sandwich Enzyme Immunoassay with Monoclonal Antibodies to Human Alpha-Fetoprotein", *J. of Immunological Methods*, 42, pp. 11-15 (1981).

*Primary Examiner*—David Saunders
*Attorney, Agent, or Firm*—Staas & Halsey

[57] ABSTRACT

A lyophilized mixture of reactants for an immunoassay includes antibody-gold sol particle conjugates, antibody latex particle conjugates, polyethylene glycol, a polyethylene glycol p-isooctylphenyl ether detergent and a sugar such as dextrin or trehalose. The polyethylene glycol is present to enhance binding of the immunoreactants and the polyethylene glycol p-isooctylphenyl ether detergent is present to prevent non-specific interactions. The sugar prevents agglomeration of the polyethylene glycol and polyethylene glycol p-isooctylphenyl ether in the lyophilized mixture at room temperature and facilitates retention of a homogenous distribution of the ingredients of the mixture to thereby enhance shelf life and redistribution of the mixture in an aqueous test system.

12 Claims, No Drawings

IMMUNOASSAY INCLUDING LYOPHILIZED REACTANT MIXTURE

RELATED APPLICATION

This application is a Continuation-In-Part of application Ser. No. 275,656, filed Nov. 21, 1988 (now U.S. Pat. No. 4,931,385), which in turn is a Continuation of application Ser. No. 747,605, filed June 24, 1985 (now abandoned). The entireties of the disclosures of said prior applications are hereby specifically incorporated by reference.

BACKGROUND OF THE INVENTION

1. Field of the Invention

The present invention relates to immunoassays and immunoassay techniques for the detection of bindable substances, such as antibodies and antigens, and in particular to improved lyophilized reactant mixtures for use therewith. More particularly, the invention relates to improved materials and methodology for use in connection with either the ELISA procedures and materials disclosed in said '656 application, filed Nov. 21, 1988, or the metal sol capture immunoassay procedures and kits disclosed in co-assigned and co-pending U.S. application, Ser. No. 105,285, filed Oct. 7, 1987 (now U.S. Pat. No. 4,859,612). and Ser. No. 177,114, filed Apr. 4, 1988. The entireties of the disclosures of the '285 and '114 applications are also hereby specifically incorporated by reference. Additionally, the disclosure of the '285 application provides an excellent description of prior developments in the field of diagnostic procedures based on immunochemistry and reactions.

2. Description of Prior Activities and Developments

In accordance with certain specific procedures disclosed in said '285 application and in said '114 application, antibody-gold sol particle conjugates and antibody-solid phase particle conjugates are dispersed together in an aqueous system containing human urine. In accordance with certain specific procedures disclosed in said '656 application, of which the present application is a Continuation-In-Part application, antibody-enzyme conjugates are dispersed in an aqueous system containing human urine. When such materials are to be utilized for testing at a place or time that is remote from the place or time where the reactants are prepared, suitable methodology must be employed to ensure the preservation of the reactants and the physical retention of the characteristics thereof which permit the same to be readily dispersed in an aqueous system, particularly one which is made up predominately of human urine.

Lyophilization, or freeze drying as the procedure may be more commonly known, may be used to preserve the ingredients and components for use in procedures such as those which are utilized in the conduct of immunoassays. It is important, however, that the lyophilization procedure results in a homogenous distribution of the components of a multi-component mixture and that the lyophilized mixture remains homogenous and in a readily utilizable form during the storage period. In particular it is important that the lyophilized, solid state materials are readily dispersible upon contact with the test materials to immediately produce a solution and/or dispersion wherein the various components and ingredients are essentially either in solution or in a monodispersed condition.

As described in said '656 application, it is sometimes advantageous to conduct an immunoassay procedure in the presence of binding enhancing agents to enhance formation of an immune complex and/or surfactants (or detergents) which operate to suppress non-specific interactions. Generally speaking, the binding enhancing agents and the surfactants comprise organic materials that are liquid at room temperature, and such materials should, for optimum benefits, be dispersed generally homogeneously throughout the reaction system.

As indicated above, lyophilized materials are often utilized in connection with immunoassay materials to preserve and protect the components, particularly during storage for long periods of time. And it is desirable that a single lyophilized mixture of materials be provided and which is readily dispersible in aqueous solution to supply all of the ingredients which desirably are present in the reaction system during the immunoassay period. However, it has been determined that liquid organic materials which enhance the performance of assays by performing as binding enhancing agents or as surfactants which suppress non-specific interactions are not readily incorporatable into lyophilized mixtures of materials because of their tendency to agglomerate at room temperature and disrupt the homogeneity of the lyophilized mixture. Such normally liquid organic components tend to agglomerate at room temperature to form liquid globules that not only interfere with the shelf life of the lyophilized mixture but prevent the redistribution of the lyophilized ingredients into an aqueous system when the time for conducting the immunoassay procedure has come. Accordingly, in the past it has been difficult to provide kits which include a single lyophilized mixture of materials which, upon reconstitution in an aqueous medium, supplies all of the materials which are desirably present in the reaction milieu.

SUMMARY OF THE INVENTION

The present invention addresses the problem of providing lyophilized mixtures of materials which may be readily reconstituted in an aqueous media to present a reaction system containing all of the ingredients necessary for the conduct of an immunoassay procedure. In accordance with the present invention, the lyophilized mixture includes a component which essentially retards or inhibits the tendency of liquid organic components such as binding enhancing agents and non-specific interaction suppressing detergents to agglomerate and thus disturb the homogeneity of the lyophilized mixture. Thus, the invention provides a lyophilized mixture for use in an immunoassay procedure. The mixture comprises at least one dispersible immunoreactive component which is distributed homogeneously throughout the lyophilized mixture. The mixture further includes at least one normally liquid organic component which is also distributed homogeneously throughout the mixture, such organic component having a property which enhances the performance of the immunoassay by its presence. Additionally, the lyophilized mixture of the present invention includes a sugar comprising dextrin or trehalose, and such sugar is present in the mixture in sufficient quantity to prevent agglomeration of the organic component to thus maintain the homogeneity of the mixture to thereby facilitate storage and shelf life of the mixture and the eventual dispersion of the mixture in an aqueous medium for the conduct of an immunoassay procedure.

In accordance with the invention, the immunoreactive component may comprise an antibody conjugate such as an antibody-gold sol particle conjugate, an antibody-solid carrier particle conjugate or an antibody-enzyme conjugate.

In one form of the invention, the organic component may comprise a binding enhancing agent such as a non-ionic, water soluble polymer. Suitable materials for use as a binding enhancing agent include polyethylene glycol, polyvinyl alcohol, polyvinyl pyrrolidone and dextran, and polyethylene glycol is a particularly preferred binding enhancing agent.

In another aspect of the invention, the organic component may comprise a water soluble non-ionic surface active agent. A number of such agents are known to those skilled in the art. In accordance with the invention, a particularly preferred material comprises a polyethylene glycol p-isooctylphenyl ether compound.

Often the lyophilized mixture may include two normally liquid organic components, one of which comprises a binding enhancing agent and the other of which comprises a surfactant. And in the preferred form of the invention wherein two organic components are involved, the binding enhancing agent may comprise a polyethylene glycol and the surfactant may comprise a polyethylene glycol p-isooctylphenyl ether compound.

DETAILED DESCRIPTION OF THE PREFERRED EMBODIMENTS

As set forth above, the present invention provides a lyophilized mixture which is readily reconstitutable in aqueous solution to supply the ingredients necessary for conducting an immunoassay procedure. The immunoassays which are particularly facilitated through the use of the present invention are those which result in the formation of a sandwich form immunocomposite. Thus, the present invention has great utility in connection with the sol capture procedures described in said '285 and '114 applications. The sol capture assays involve a first antibody coated onto a solid carrier particle and a second antibody coated onto a metal sol label particle. Such antibody-particle conjugates are then incubated with a test solution containing an analyte (usually human urine) to allow immunoreaction of the components and the resultant production of a collectible immunocomposite containing the metal sol label particles. In such assays, the labelled immunocomposite is collected and inspected visually and the color thereof resulting from the incorporation therein of the metal sol label particles is detectable with the naked eye.

One of the important aspects of the gold sol methodology is that all of the reactions necessary to form the detectable immunocomposite may proceed simultaneously in a single reaction vessel. To prepare the components, a first antibody is absorbed onto a solid carrier particle and a second antibody is absorbed onto a metal sol label particle. The test solution suspected of containing a bindable analyte is incubated with the antibody conjugates simultaneously and the immunocomposite formed if the test is positive is collected. The collected materials are visually inspected for the presence of metal sol coloration in the collected solid phase. In the conduct of such an immunoassay, it is preferable to provide an admixture of the antibody conjugates and to then admix the test solution with the mixture of conjugates. The resultant admixture may then be incubated for a prescribed period under ambient room temperature conditions between about 15° C. to less than about 37° C. The mixture may then be poured onto a porous membrane filter where the immunocomposite may be collected for inspection while liquid materials and unbound labelled antibody conjugates simply flow through the membrane and are subsequently discarded. Typically the analyte is an antigen. Both the first and second antibodies may be polyclonal antibodies; however, preferably at least one of the first and second bodies is a monoclonal antibody. And in the most preferred case, the antibodies are two different monoclonal antibodies specific for respective different epitopes on the antigen molecule. In a particularly preferred form of the invention, a gold sol particle is utilized to provide a visual indication of the presence of bound components on the collection membrane.

Pursuant to the invention, the present invention facilitates the provision of kits and components that are particularly suitable for home and clinical diagnostic applications and which are implementable by unskilled users without specialized equipment. In particular the invention provides immunologic reagents which may be stored for prolonged periods without losing their reactivity, immunologic binding specificity or avidity even though the same may have been exposed to hot, humid environmental conditions during transit, or prior to use in the assay. Moreover, the reagents remain in a condition which facilitates the immediate reconstitution thereof in urine or other aqueous test samples to present complete reaction systems. Thus, the invention provides a lyophilized product mixture which may contain an antibody-metal sol particle conjugate, one of the active immunologic reagents utilized in the sol capture assay. The lyophilized product may also contain an antibody-solid phase carrier particle conjugate. In addition to the two antibody-particle conjugates, the lyophilized product mixture may preferably contain additives which are desirably present in the reaction system.

To prepare the lyophilized mixture, the desired ingredients are first all blended in an aqueous lyophilization phase. The lyophilization phase containing the conjugates and additives is subjected to freeze drying to form a powered, lyophilized (freeze dried) product. The effect of the lyophilized product mixture of the invention containing the antibody-particle conjugates is multiple. The additives to be included in admixture with the antibody-particle conjugates in the lyophilized product may be chosen for their ability to preserve the reactivity, binding specificity and avidity of the antibodies when applied to the assay even if the lyophilized product containing the antibody conjugates should be subjected to hot environmental conditions between 80° F. to 120° F. In practical terms this means that antibody conjugates can be included in diagnostic kits without concern that the reactivity or immunologic binding specificity of the antibodies will be lost if the kit components are exposed to hot, humid environmental conditions. Additionally, the user may feel free to store the lyophilized product containing the conjugate at ambient conditions without the need for refrigeration and with no need for concern if environmental conditions become hot or humid.

Importantly, the lyophilized mixture has the ability to retain its homogeneity even though it contains one or more organic components which are normally liquids at room temperature and which therefore might ordinarily agglomerate subsequent to lyophilization when the lyophilized mixture is warmed to room temperature to thereby disrupt the homogeneity of the freeze dried mixture.

Lyophilized mixtures of materials facilitate the reduction of the total number of components needed for application of the procedure to home diagnostic use. Thus, a preferred diagnostic kit which incorporates the ingredients useful in connection with the sol capture procedure need include only a vial of lyophilized product containing antibody-particle conjugates and other reaction ingredients; a measuring dispenser such as an eye dropper; and an immunocomposite collection and inspection device. Using the measuring dispenser, the user need only dispense a required amount of sample (e.g., urine, suspected of containing a target antigen) in the vial of the lyophilized product containing the conjugates. The mixture may then be allowed to incubate for a prescribed period of time at room temperature. The resultant immunocomposite (if the test is positive) may then be collected using the collection device and the collected mass may be inspected for the color characteristic of the metal sol particle.

The simplicity of such diagnostic kit stems in part from the fact that all of the desirable or required additives for the reaction procedure have been incorporated into the lyophilized product mixture containing the conjugates. In this regard, it has been discovered that normally liquid organic components such as binding enhancing agents to enhance formation of immune complexes and detergents to suppress non-specific interactions may be distributed homogeneously throughout the lyophilized mixture and prevented from agglomeration at room temperature simply by incorporating a sugar comprising dextrin or trehalose into the solution prior to lyophilization. Upon lyophilization the sugar has the ability to prevent agglomeration of the organic component and thus to maintain the homogeneity of the mixture and thereby facilitate storage and shelf life of the mixture and the eventual dispersion of the mixture in an aqueous medium for conduct of the immunoassay procedure. As a result of the incorporation of the sugar in the lyophilized mixture, the immunoreactive components and the liquid organic components remain distributed homogeneously throughout the mixture during storage. As a result of the presence of the sugar and the resultant even distribution of the organic liquids in the lyophilized mixture, the reactivity, binding specificity and avidity of the immunoreactive component are retained and the lyophilized mixture retains its ability to be readily dispersed upon subsequent contact with an aqueous system.

A normally liquid organic component which desirably is included in the lyophilized mixture comprises a binding enhancing agent capable of accelerating formation of immune complexes from the conjugates. The binding enhancing agent may preferably be a non-ionic water soluble polymer such as polyethylene glycol, polyvinyl alcohol, polyvinyl pyrrolidone or dextran. Polyethylene glycol has found to be the optimum binding enhancing agent for utilization in the sol capture procedures of the '285 and '114 applications and in the enzyme assay described in said '656 application.

As set forth above, the lyophilized mixture may preferably include all of the ingredients which desirably are present in the reaction system for the immunoassay. Thus, the lyophilized mixture may include buffer components selected to provide a pH of about 7.8 to 8.2 in the reaction milieu. Preferred buffer components, particularly for purposes of the sol capture procedures, include Tris base. Additionally, the system may advantageously include chelating agents such as EDTA disodium to tie up the divalent cations often present in urine. Other chelating agents such as ethylene diamine tetraacetic acid (EDTA), citric acid, tartaric acid, glucuronic acid, saccharic acid or suitable salts of these acids are enumerated in U.S. Pat. No. 4,228,240 and could possibly be substituted for EDTA disodium. However, in the context of the present invention, EDTA disodium is preferred for use with urine test samples.

In accordance with the invention it has been found that oligosaccharides, preferably containing disaccharides (but not sucrose) and more preferably containing dextrin or trehalose sugars are important components in the lyophilization mixture for achieving the benefits of the present invention. Thus, when such sugars are present in the mixture in sufficient quantity, agglomeration of the binding enhancing agent and/or the surfactant is prevented and thus the homogeneity of the mixture is maintained. Accordingly, storage and shelf life of the mixture and the eventual dispersion of the mixture into an aqueous medium for conduct of an immunoassay procedure are facilitated.

The criticality associated with the selection of the specific class of sugars is surprising. It has been determined that the appropriate class of sugars includes members that exhibit a number of unique properties simultaneously. The appropriate sugars must be rapidly soluble in water, preferably dissolving in less than one minute. The sugars must also have the property that provides a visually homogeneous, stable solid mixture, i.e., a homogeneous stable matrix, of the lyophilized product containing the conjugates. Discovery of suitable sugars having the requisite combination of properties was difficult. Most sugars and also sucrose have been found to be unsatisfactory because they do not produce a homogeneous stable, solid mixture, i.e., a stable homogeneous matrix upon lyophilization, but instead produce lyophilized mixtures having concentration gradients for the individual components. The concentration gradients are believed to be the result of the agglomeration of the organic components at room temperature due to the fact that these components are normally liquid at room temperature. Such agglomeration results in the destruction of the homogeneity of the mixture and the resultant production of concentration gradients therein. The concentration gradients tend to have a deleterious effect on the conjugated antibodies caused by a more direct and concentrated exposure of the same to the agglomerated liquid globules in the lyophilized product. A suitable commercial product consisting of dextrins is available under the trade name MALTRIN from Grain Processing Corp.

The surface active agent (surfactant) for use in the mixture, and which may often be characterized as a detergent, may be selected from the class of water soluble non-ionic surface active agents. The surfactant may be selected from a wide variety of soluble non-ionic surface active agents. However, it has been determined that the most suitable surfactants are generally commercially available under the IGEPAL trade name from GAF Company. The IGEPAL liquid non-ionic surfactants are polyethylene glycol p-isooctylphenyl ether compounds and are available in various molecular weight designations, for example, IGEPAL CA720, IGEPAL CA630, and IGEPAL CA890. Other suitable non-ionic surfactants include those available under the trade name TETRONIC 909 from BASF Wyandotte Corporation. This material is a tetrafunctional block copolymer surfactant terminating in primary hydroxyl groups. Other suitable non-ionic surfactants are available under the VISTA ALPHONIC trade name from Vista Chemical Company and such materials are ethoxylates that are non-ionic biodegradables derived from linear primary alcohol blends of various molecular weights. Such non-ionic surfactants are most suitable for the purposes of the invention because they provide an appropriate amount of detergency for the assay without having a deleterious effect on the conjugate. In particular such surfactants are included in the reaction mixture for the purpose of suppressing non-specific interactions among the various ingredients of the immunoassay reaction system, and in this connection IGEPAL CA720 is a particularly preferred surfactant or detergent.

In view of the extreme sensitivity of the immunologic components to both environmental conditions and chemical environments, the difficulty of achieving a lyophilized product having the properties described herein should be clear. By the inclusion of the surfactant in the lyophilized product, the need for including a detergent as a separate kit component is eliminated.

The prior art teaches that surfactants such as detergents should normally be kept separated from immunoreactants. This is due to the fact that immunoreactants often are sensitive to detergents and surfactants and exposure to such materials often effects the binding properties of the immunoreactants. The same is true of binding enhancing agents such as polyethylene glycol, that is, exposure of immunoreactants to polyethylene glycol may effect the binding properties of the immunoreactant. However, in accordance with the present invention, it has been bound that the presence of a sugar comprising dextrin or trehalose in the lyophilized mixture eliminates or at least minimizes the effect of such ingredients on the binding properties of the immunoreagents. This may be the result of the property of the sugar which prevents agglomeration of the organic component and keeps it distributed homogeneously throughout the mixture in essentially a monodispersed form. Thus, the presence of the sugar may effectively retard contact between the liquid organic components and the immunoreactive components which are distributed homogeneously throughout the lyophilized mixture. In any event, it has been a surprising discovery that when a sugar comprising dextrin or trehalose is present in the lyophilized mixture in sufficient quantity, agglomeration of the organic component is prevented and the homogeneity of the mixture is maintained whereby storage and shelf life of the mixture and the eventual dispersion of the mixture in an aqueous medium for conduct of the immunoassay procedure are each facilitated. Additionally, the immunoreactive components distributed homogeneously throughout the lyophilized mixture do not lose their binding properties even though the mixture may be exposed to hot ambient conditions and stored for substantial periods of time.

The present invention provides a lyophilized mixture suitable for use with the sol capture assays described in said '285 and '114 applications. Additionally, the lyophilized mixture of the present invention is useful in connection with the ELISA type immunoassays described fully in said '656 parent application. These assays are advantageously employed for the detection of particular antigens or antibodies which may be present in unknown concentrations in test samples. The immunoassay with which the lyophilized mixtures of the present invention may be employed are applicable to the measurement of a wide variety of specific antigens and antibodies and they have been found to have particular utility in home diagnostic kits for detection of antigens such as human chorionic gonadotropin hormone (hCG) which is present in the urine of pregnant women. The lyophilized mixture of the present invention may also be utilized in connection with assays for the detection of Neisseria gonorrhea, the bacteria causing gonorrhea, also called gonococcus (GC) and human luteinizing hormone (hLH), a hormone that is present in female urine at the time of ovulation.

As set forth above, the present invention provides a lyophilized mixture which has great utility in connection with the sol capture procedures described in the '285 and '114 applications identified above. Thus, the lyophilized mixture includes two dispersible immunoreactive components, one of which is an antibody-gold sol particle conjugate and the other of which is an antibody-solid carrier particle conjugate. The preparation of such conjugates is fully described in said '285 application. In this preferred embodiment of the invention, the lyophilization mixture also should contain both a polyethylene glycol binding enhancing agent and a polyethylene glycol p-isooctylphenyl ether surface active agent to suppress non-specific interactions between the various components of the reaction mixture. Preferably the preferred lyophilized mixture may also contain a Tris base buffering agent to control pH, and an EDTA disodium salt as a chelating agent to tie up divalent cations from human urine. Thimerosal may be included as an anti-bacterial agent to improve shelf life prior to freeze drying and in this sense it should be recognized that the thimerosal is present in the freeze dried product not so much because of its effect on the lyophilized mixture but more so because of its effect on the material prior to freeze drying.

In accordance with the invention, to prepare an appropriate lyophilized mixture for use in a gold sol capture procedure, the solution to be subjected to lyophilization may contain materials suitable for detecting the presence of hCG using assay procedures which are generally the same as those described in Examples IV(f) and (g) of said co-pending '285 application. The antibody coated gold sol particles may be prepared essentially as set forth in the prior application and preferably the gold sol particles should have a diameter of approximately 30 nm. (See, G. Frens, Nature 241, 20–22, (1973)). The preferred antibody for coating the gold sol particles is the 2G9 antibody described in said prior '285 application. The antibody coated gold sol particles may be processed as set forth in the '285 application to produce a final product which comprises a suspension of the gold labelled probe particles and which may then be used as the labelled component in the preferred immunoassay of the invention. Thus, the labelled component comprises the 2G9 antibody conjugated to an appropriate amount of 30 nm gold sol particles.

In the preferred form of the invention, the assay procedure further involves the use of a solid phase component which comprises the coupling product of a second antibody and a solid phase particle. The second antibody is also an antibody to hCG and the same is referred to as 2B2 antibody in said '285 application. In accordance with this preferred aspect of the invention the 2B2 antibody and the 2G9 antibody are specifically immunoreactive with respect to different sites or epitopes on the hCG molecule. That is to say, 2B2 antibody reacts with the hCG molecule at one specific epitopic site, while the 2G9 antibody reacts with the hCG molecule at a different, spatially removed specific epitopic site. Thus, when the test is positive, a composite made up of the gold sol particle, the 2G9 antibody, the hCG molecule, the 2B2 antibody and the solid phase particle is formed. Such composite is sufficiently large to be captured on a filter element where the inherent and distinctive coloration of the bound gold sol particles may be visually observed.

The 2B2 antibody-solid carrier particle conjugate for use in connection with the preferred form of the invention may be prepared using any of the various methods and materials disclosed and described in said co-pending '285 application. Thus, 2B2 antibody-latex probe particles are prepared by conjugating the 2B2 antibodies to $0.99\mu$ carboxylated modified latex particles.

In accordance with the present invention, an admixture of freeze dried antibody-latex particle conjugates and freeze dried antibody-gold sol particle conjugates may be provided in a single test container (or vial) containing an amount of each conjugate needed for conducting a single test. The admixture of freeze dried antibody-particle conjugates may be prepared by forming a single dispersion containing both species of conjugates and freeze drying the conjugates together. This provides a simplified kit for commercial purposes. Additionally, the other ingredients to be included in accordance with the immunoassay may be incorporated in the lyophilized mixture in the test container at this time.

Each individual test should preferably contain gold probe particles consisting of about 2.75 $\mu$g of 2G9 antibody conjugated to about 0.27 $OD_{533nm}$ units of 30 nm gold sol particles, latex probe particles consisting of about 6.0 $\mu$g of 2B2 antibody conjugated to about 1.0 $OD_{500nm}$ units of $0.99\mu$ carboxylated modified latex particles. To prepare a lyophilized mixture from such immunoreactive components, a single aqueous system is provided and which includes the various components necessary or desirable in the immunoassay procedures. Thus, 500 ml of an aqueous system to be subjected to freeze drying is prepared. The system preferably contains 2.75 mg of the 2G9 antibody conjugated to gold sol particles; 6.0 mg of the 2B2 antibody conjugated to carboxylated modified latex particles; 10.0 mg of polyethylene glycol (20M) as a binding enhancing agent; 48 mg of thimerosal; 5.8 gms of Tris base buffer; 48 gms of Maltrin; 1.44 gms of EDTA disodium salt and 0.144 ml of IGEPAL CA720. The liquid system comprises a solution of soluble materials and a dispersed suspension of non soluble materials such as the antibody-particle conjugates. The resultant dispersion, which contains sufficient ingredients for the conduct of approximately 1000 test procedures, is distributed equally among 1000 glass lyophilization vials and subjected to conventional freeze drying procedures.

The lyophilization cycle which has been found to be preferable requires the initial freezing of the aqueous lyophilization dispersion containing the conjugate. The dispersion is frozen in a conventional lyophilization chamber maintained at a temperature range between about $-40°$ C. and $-35°$ C. for at least 2 hours at atmospheric conditions. The frozen lyophilization dispersion containing the antibody-particle conjugates is subjected to a vacuum of about 10 to 50 milli torr over a 24 hour period. During this 24 hour cycle the temperature in the lyophilization chamber is adjusted to incremental levels while the high vacuum conditions are maintained at about 20 to 50 milli torr. Typical temperature levels employed during the lyophilization cycle are $-10°$ C. for 18 hours; and $+25°$ C. for about 7 to 10 hours until the product reaches about 25° C. The lyophilization chamber is then partially filled with nitrogen and the vials containing the lyophilized product are stoppered. During the lyophilization cycle, the liquid initially contained in the lyophilization dispersion evaporates. The resulting lyophilized product containing antibody-particle conjugates comprises a lyophilized mixture and the various ingredients thereof are distributed homogeneously throughout the mixture.

As desired, the dispersion to be subjected to freeze drying may contain other ingredients which are desirably present during the conduct of the immunoassay. Thus, a green dye as described in said '114 application, may be included in the dispersion to be subjected to freeze drying whereby the green dye will be present in the lyophilized mixture.

The lyophilization vials subjected to lyophilization, as set forth above, each contain a lyophilized mixture for use in an immunoprocedure. The mixture comprises two dispersible immunoreactive components distributed homogeneously throughout the mixture. One of the dispersible immunoreactive components is the 2B2 antibody conjugated to $0.99\mu$ carboxylated modified latex particles, and the other of the immunoreactive components comprises the 2G9 antibody conjugated to 30 nm gold sol particles. The lyophilized mixture in the lyophilization vial also includes two normally liquid organic components, the first of which comprises the IGEPAL CA720 detergent and the other of which comprises polyethylene glycol (20M). As set forth above, the IGEPAL component is included to inhibit non-specific interactions between the components of the system. And the polyethylene glycol is present to enhance the binding activity of the immunoreactants. The amounts of these materials is not a critical feature of the present invention; however, the same need to be present in amounts which are deemed either necessary or desirable to achieve the sought after results, and suffice it to say, the present invention provides a mechanism for diminishing and/or eliminating the undesirable results which otherwise might be experienced when the liquid organic components are used.

The lyophilized mixture in the lyophilization vial also contains the sugar. Each vial contains approximately 48 $\mu$g of Maltrin, an amount determined empirically to prevent agglomeration of the 0.144 $\mu$l of IGEPAL CA720 and the 10.0 $\mu$g of PEG present in each lyophilization vial. However, it should be recognized that the amount of the sugar is not critical other than that the same must be present in an amount which is sufficient to prevent agglomeration of the normally liquid components whereby the homogeneity of the mixture is maintained and the storage and shelf life and eventual dispersion of the mixture in an aqueous medium are both facilitated. As will be appreciated by those of ordinary skill in the art to which the present invention pertains, the optimum amount of the sugar to be included in any given mixture of ingredients will depend on a number of unrelated phenomena and must generally be determined empirically. In this regard, the agglomeration of the liquid organic components will simply cause the lyophilized mixture to have paste like rather than particulate characteristics and the determination of a correct amount of sugar to achieve the desired particulate characteristics will not be difficult for the ordinary experimenter in the relevant art.

The lyophilized mixture of the present invention has been utilized successfully in the performance of the immunoassays described in said '285 and '114 applications. To conduct such immunoassays, the lyophilized mixture is simply contacted with 0.4 ml of urine and the lyophilized mixture quickly disperses in the urine in a matter of a few seconds.

We claim:

1. A lyophilized mixture for use in an immunoassay procedure comprising:
    at least one dispersible immunoreactive component distributed homogeneously throughout said mixture;
    at least one organic component distributed homogeneously throughout said mixture, said organic component normally being a liquid at the conditions under which the mixture is stored or retained prior to use and having a property which enhances the performance of the immunoassay by its presence; and
    a sugar comprising dextrin or trehalose, said sugar being present in said mixture in sufficient quantity to prevent agglomeration of the organic component and thus maintain the homogeneity of the mixture to thereby facilitate storage and shelf life of the mixture and the eventual dispersion of the mixture in an aqueous medium for conduct of the immunoassay procedure.

2. A lyophilized mixture as set forth in claim 1, wherein said immunoreactive component comprises an antibody conjugate.

3. A lyophilized mixture as set forth in claim 2, wherein said antibody conjugate comprises an antibody-enzyme conjugate.

4. A lyophilized mixture as set forth in claim 1, wherein said organic component comprises a binding enhancing agent.

5. A lyophilized mixture as set forth in claim 4, wherein said binding enhancing agent comprises a nonionic, water soluble polymer.

6. A lyophilized mixture as set forth in claim 5, wherein said polymer comprises polyethylene glycol.

7. A lyophilized mixture as set forth in claim 5, wherein said polymer comprises polyvinyl alcohol.

8. A lyophilized mixture as set forth in claim 5, wherein said polymer comprises polyvinyl pyrrolidone.

9. A lyophilized mixture as set forth in claim 5, wherein said polymer comprises dextran.

10. A lyophilized mixture as set forth in claim 1, wherein, said organic component comprises a surfactant.

11. A lyophilized mixture as set forth in claim 10, wherein said surfactant comprises a water soluble nonionic surface active agent.

12. A lyophilized mixture as set forth in claim 11, wherein said surface active agent comprises a polyethylene glycol p-isooctylphenyl ether compound.

* * * * *